US006928312B2

(12) United States Patent
Todd et al.

(10) Patent No.: US 6,928,312 B2
(45) Date of Patent: Aug. 9, 2005

(54) ELECTRODE HAVING WIRE CONNECTED THERETO AND METHOD FOR ASSEMBLING SAME

(75) Inventors: William A. Todd, Indianola, IA (US); Lorne C. Scharnberg, West Des Moines, IA (US)

(73) Assignee: Katecho, Inc., Des Moines, IA (US)

( * ) Notice: Subject to any disclaimer, the term of this patent is extended or adjusted under 35 U.S.C. 154(b) by 515 days.

(21) Appl. No.: 10/259,085

(22) Filed: Sep. 27, 2002

(65) Prior Publication Data

US 2004/0064178 A1 Apr. 1, 2004

(51) Int. Cl.$^7$ ................................................. A61N 1/05
(52) U.S. Cl. ...................... 600/372; 607/115; 607/142; 607/152
(58) Field of Search ................................. 600/372, 382, 600/386, 391–394; 607/115, 37, 142, 152, 153; 439/909; D24/168, 187

(56) References Cited

U.S. PATENT DOCUMENTS

| 4,996,989 A | * | 3/1991 | Stundel et al. | 600/383 |
| 5,456,710 A | * | 10/1995 | Gadsby | 607/142 |
| 6,091,977 A | * | 7/2000 | Tarjan et al. | 600/372 |

* cited by examiner

*Primary Examiner*—Kennedy Schaetzle
(74) *Attorney, Agent, or Firm*—McKee, Voorhees & Sease, P.L.C.

(57) ABSTRACT

A connector for connecting a wire to an electrode includes a rigid body which presses downwardly against the wire and presses it into contact with the laminated sheet member of the electrode. The body includes first and second pairs of spaced apart prongs and third and fourth prongs, all of which pierce the laminated sheet member and are bent upwardly into contact with the central portion of the connector.

17 Claims, 5 Drawing Sheets

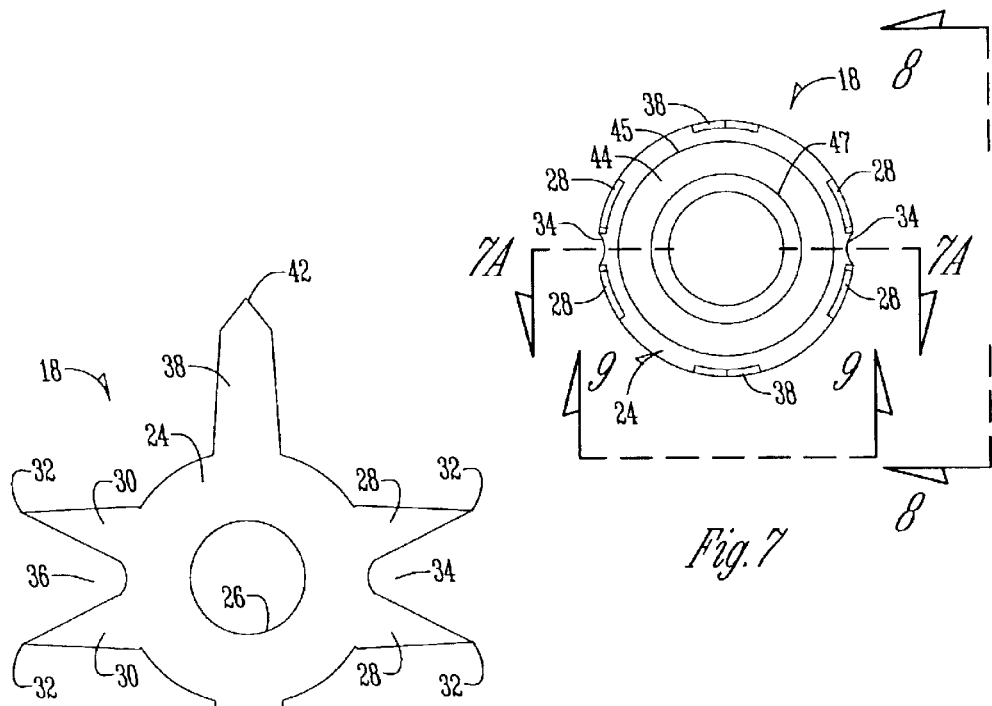
Fig. 7
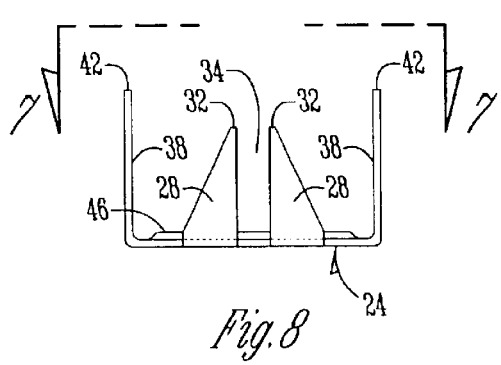
Fig. 6
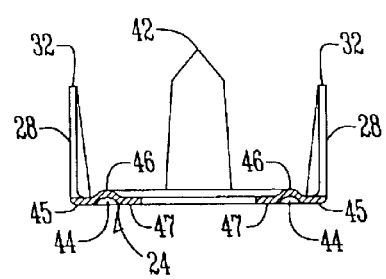
Fig. 7A
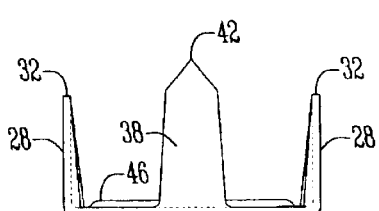
Fig. 9
Fig. 8

ELECTRODE HAVING WIRE CONNECTED THERETO AND METHOD FOR ASSEMBLING SAME

BACKGROUND OF THE INVENTION

This invention relates to an electrode having wire connected thereto and method for assembling same.

Various types of physiological electrodes have been utilized. One type of electrode is a stimulating electrode which attaches to a patient's skin and stimulates the skin by applying electrical current. These stimulating electrodes may be utilized for stimulating muscles, for fibrillating a patient's heart, or for pacing a patient's heart beat.

Another type of electrode is a monitoring electrode which is attached to the patient's skin and which receives small electrical impulses emanating from the patient and conveys those impulses to a monitor or screen. Examples of these types of electrodes are electro cardiogram electrodes. Often stimulating electrodes include monitoring capability as well and these types of electrodes must meet the criteria for both stimulating the patient and for monitoring electrical impulses emanating from the patient.

These types of electrodes usually include a sheet member which attaches in some manner to the patient's skin. The sheet member is usually laminated and includes a conductive portion to which is attached a wire. The wire either delivers current to the patient's skin through the electrode or receives the electrical impulses from the patient through the electrode.

It is important that a very good electrical connection be made between the wire and the conductive sheet member. Various types of connectors have been used for this purpose. The present invention is believed to present an improved connection between the wire and the conductive sheet member of the electrode.

Therefore a primary object of the present invention is to provide an improved electrode having a wire connected thereto and method for assembling same.

A further object of the present invention is the provision of an electrode having an electrical connector which assures positive electrical contact between the wire and the electrode at all times.

A further object of the present invention is the provision of an electrode having an electrical connector which maintains electrical contact throughout various movements of the wire, the patient, or the electrode, including a pulling action on the wire.

A further object of the present invention is the provision of an improved electrode having an electrical connector which places the wire in direct contact with the conductive upper layer of the electrode and which holds the wire in that direct contact.

A further object of the present invention is the provision of an improved electrode having a connector which is economical and efficient to manufacture.

A further object of the present invention is the provision of electrode having an electrical connector that provides improved pull strength when the wire is pulled in a direction away from the electrode.

A further object of the present invention is the provision of an electrode having an electrical connector which provides a more reliable electrical interface.

A further object of the present invention is the provision of an electrode having an electrical connector which provides a thinner profile, a lighter weight, and fewer parts.

A further object of the present invention is the provision of a method for assembling an electrode, including a method for connecting the wire to the electrode which is simple, repeatable, and reliable in operation.

BRIEF SUMMARY OF THE INVENTION

The foregoing objects may be achieved by an electrode comprising a laminated sheet having a hydrogel layer of tacky electrical conductive material, an electrically conductive layer, and one or more additional layers. The conductive layer is between the hydrogel layer and the additional layers and is in electrical contact with the hydrogel layer.

A rigid body includes a first body surface facing the conductive layer of the laminated sheet, a second body surface opposite from the first body surface, first and second opposite body edges, and a body opening between the first and second opposite body edges. The body includes a first pair of prongs, a second pair of prongs, a third prong, and a fourth prong extending therefrom.

A wire having a bare wire portion free from insulation is positioned between the first body surface of the body and the conductive layer of the laminated sheet and is in electrical contact with the conductive layer of the laminated sheet. The bare wire portion extends across the body opening and is positioned between the first pare of spaced apart prongs and also between the second pair of spaced apart prongs. The first and second pairs of prongs and the third and fourth prongs each pierce in a first direction through the conductive layer and the additional layers and then pierce in a second direction opposite from the first direction through the additional layers and the conductive layer and contact the rigid body to attach the bare wire portion in electrical content with the conductive layer.

Accordingly to another feature of the invention the body includes spaced apart first and second convex surfaces which press the wire into contact with the conductive layer at spaced apart first and second pressure points respectively.

Accordingly to another feature of the invention the first and second pairs of prongs each include a prong end contacting the first body surface.

According to another feature of the invention the third and fourth prongs each include a prong end extending within the body opening and contacting the body surface.

According to another feature of the invention the first and second pairs of prongs each include prong ends that straddle the bare wire portion and then pinch toward one another and cover at least a part of the bare wire portion.

The method of the present invention comprises taking a connector body having a central portion comprising a first body surface a second opposite body surface a body opening extending there through, a first body edge on one side of the opening and a second body edge on the opposite side of the body opening. The body member has a first pair of prongs and a second pair of prongs each extending therefrom and each terminating in a spaced apart pair of prong ends.

The method comprises placing a bare wire free from insulation between the spaced apart prong ends of the first and second pairs of prongs and in electrical contact with a conductive layer of a sheet member. The prong ends of the first and second pairs of prongs are pierced in a first direction through the sheet member so that the bare wire is between and in electrical contact with the conductive layer of the sheet member and the first surface of the connector body. The prong ends of the first and second pairs are then pierced in a second direction opposite from the first direction through the sheet member so that the prong ends of each of the first and second pairs of prongs are on opposite sides of the bare wire. The prong ends of the first and second pairs of prongs are then pressed against a central portion of the connector body to attach the wire to the sheet member in contact with the top surface of the sheet member.

BRIEF DESCRIPTION OF THE DRAWINGS

FIG. 6 is a plan view of the connector body or connector before it has been formed into its ultimate shape.

FIG. 7 is a top plan view of the connecting body after it has been formed into its shape for application to the electrode.

FIG. 7A is a sectional view taken along line 7a—7a of FIG. 7.

FIG. 8 is a side elevational view taken along line 8—8 of FIG. 7.

FIG. 9 is a side elevational view taken along line 9—9 of FIG. 7.

DETAILED DESCRIPTION OF THE PREFERRED EMBODIMENT

Figure 1:
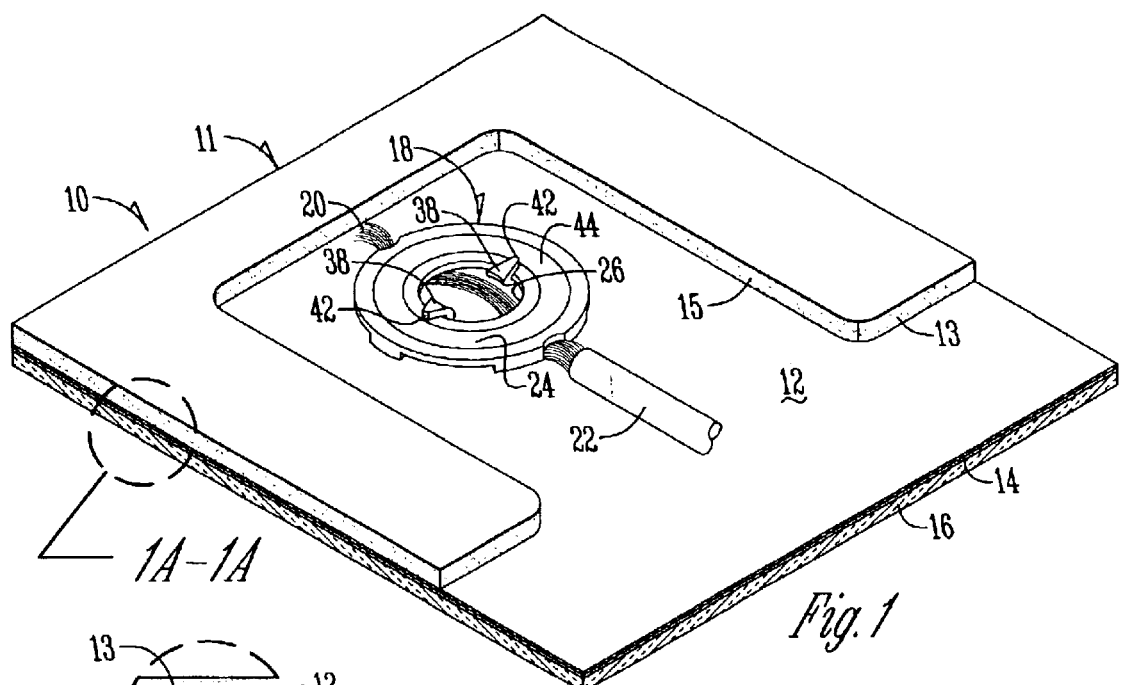
FIG. 1 is a perspective view of a portion of an electrode utilizing the connector of the present invention.
Figure 1A:
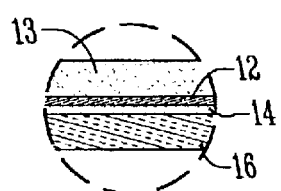
FIG. 1A is an enlarged view taken along line 1a—1a of FIG. 1
Figure 2:
FIG. 2 is a top plan view of the connector of FIG. 1.

Referring to FIGS. 1–5, the numeral 10 generally designates an electrode of the present invention. Only a portion of electrode 10 is shown. Electrode 10 includes a laminated sheet member 11 which comprises hydrogel layer 13, a tin layer 12, a tear strengthening layer 14, and a foam layer 16. Hydrogel layer 13 is a conventional hydrogel which is tacky so as to adhere to a patient's skin and which contains electrolyte so as to provide good electrical conduction between the patient's skin and tin layer 12. The tear layer 12 is a material which resists tearing, and the preferred material for this is manufactured under the trade name Tyvek®, Model No. 2FS, manufactured by EI DuPont de Nemours & Company.

Hydrogel 13 includes a cut out portion 15 in which a connector 18 connects a wire 20 to the electrode in direct contact with the tin surface 12. Wire 20 includes wire insulation 22 which extends up to the connector but is removed to expose a bare wire 20 beneath the connector 18.

Connector 18 includes a central body portion 24 having a central body opening 26 therein. As can be seen in FIGS. 6–9 the connector 18 includes a first prong pair 28 and a second prong pair 30 diametrically opposite the edges of the central portion 24. Each of the prongs in these pairs includes prong end points 32. Furthermore the prong pairs 28–30 include between the pairs a first space 34 and a second space 36 respectively. A third prong 38 and a fourth prong 40 are positioned diametrically opposite one another and are also positioned 90° away from the prong pairs 28–30. Third and fourth prongs 38–40 each include prong points 42.

FIG. 6 shows the initial blank for the connector 18. FIGS. 7–9 show the connector 18 with the prongs 28, 30, 40 and 42 bent 90° with respect to the central portion 24. The connector 18 in FIGS. 7–9 has been preformed so as to be ready to be applied to the sheet member 11. In this preformed condition the central portion 24 includes a concave ring 44 the opposite side of which is formed into a convex ring 46. Also, the preformed connector includes an outer ridge 45 and an inner ridge 47 which are positioned on the outside and inside of the concave ring 44 respectively.

Figure 3:
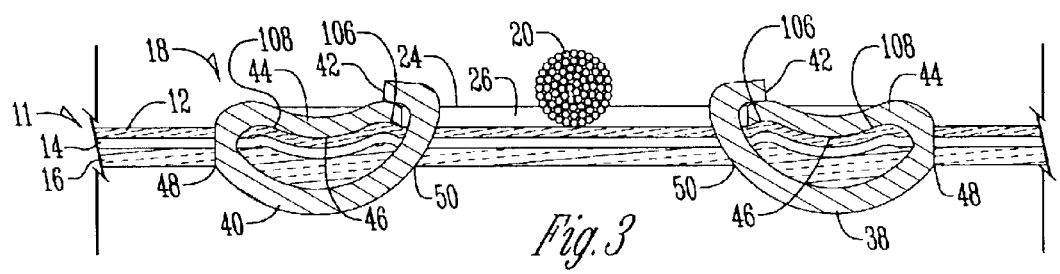
FIG. 3 is a sectional view taken along line 3—3 of FIG. 2.
Figure 4:
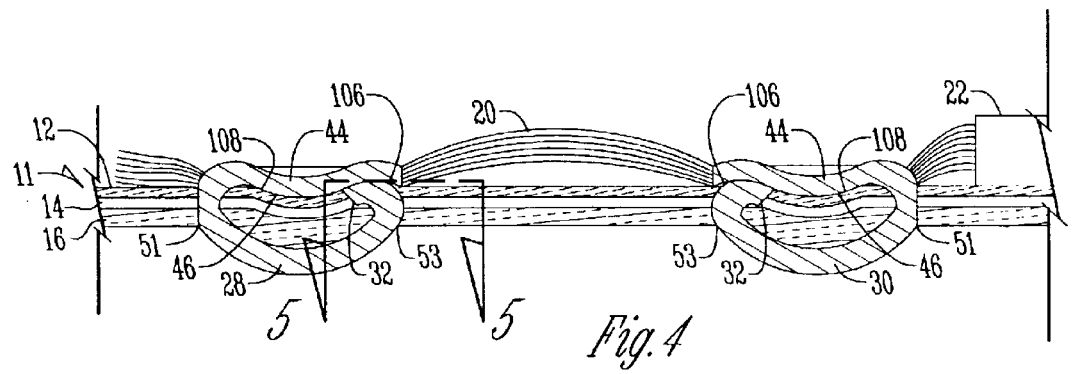
FIG. 4 is a sectional view taken along line 4—4 of FIG. 2.

FIGS. 3 and 4 show the connector 18 in its fully attached form. In this form, the third and fourth prongs 38, 40 are shown bent over and upwardly so that their tops 42 engage the upper surface of the central potion 24. The third and fourth prongs 38, 40 each extend downwardly through a first puncture hole 48 in the sheet member 11. They then extend upwardly through a second puncture hole 50 in the sheet member 11. This helps secure the connector 18 to the sheet member 11. The tight connection is further facilitated by virtue of the fact that the convex ring 46 of the connector 18 forms a downward depression in the sheet member 11.

Figure 5:
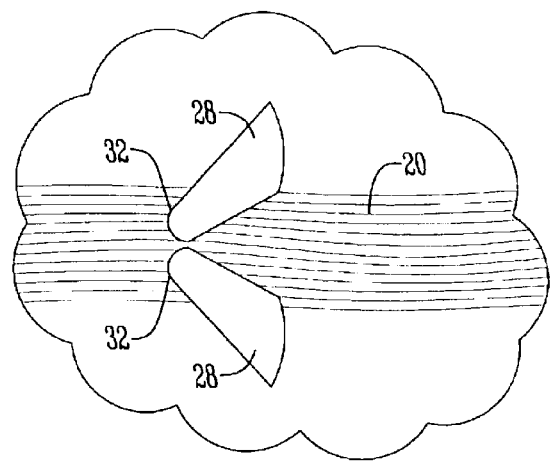
FIG. 5 is an enlarged sectional view taken along line 5—5 of FIG. 4.
Figure 10:
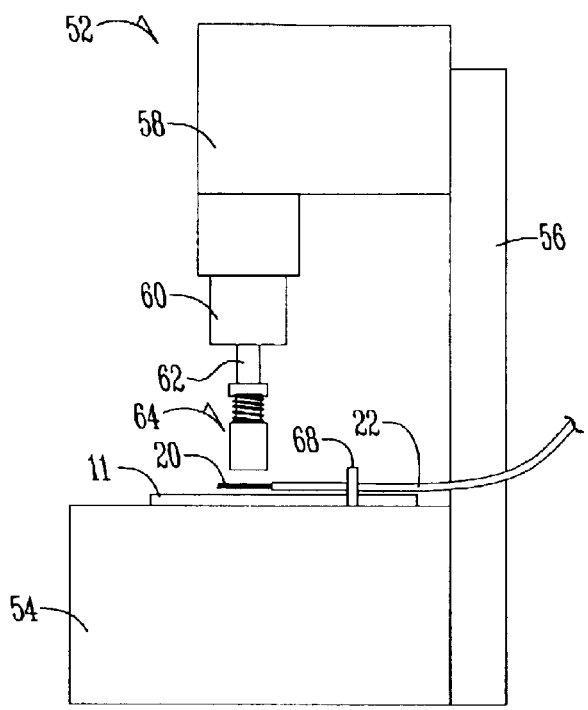
FIG. 10 is a side elevational view of a machine for applying the connector to the electrode.

FIG. 4 shows the configuration of the first and second prong pairs 28–30 after the connector 18 has been attached to the sheet member 11. In this configuration the prongs of the pairs 28–30 extend downwardly through a first puncture hole 51 and then upwardly through a second puncture hole 53. However, the tips 32 of the prong pairs 28–30 are folded on the under surface of the central portion 24 rather then on the upper surface as shown for third and fourth prongs 38–40 in FIG. 3. The tips 32 of the prongs 28–30 are shown in FIG. 5 to be overlying the wire 20. They are pressed against the under surface of the central portion 24 and are overlying the wire 20. Furthermore as shown in FIG. 5, the two prongs of each pair 28–30 are rolled over and canted inwardly in their final form so that they are pinched over the top of the wire 20. This further facilitates a strong connection to the wire 20.

Of particular importance to the pull strength of the connection provided by connector 18 are the two pinch points 106, 108 which appear at each side of the connector 18 as shown in FIG. 4. These four pinch points apply pressure between the central portion 24 and the wire 20. They force the wire downwardly into firm contact with the tin surface 12 to assure good contact with the tin surface 12. If wire 22 is pulled, there are four points 106, 108 which resist the pulling action, and therefore a very strong pull strength is provided.

Figure 11:
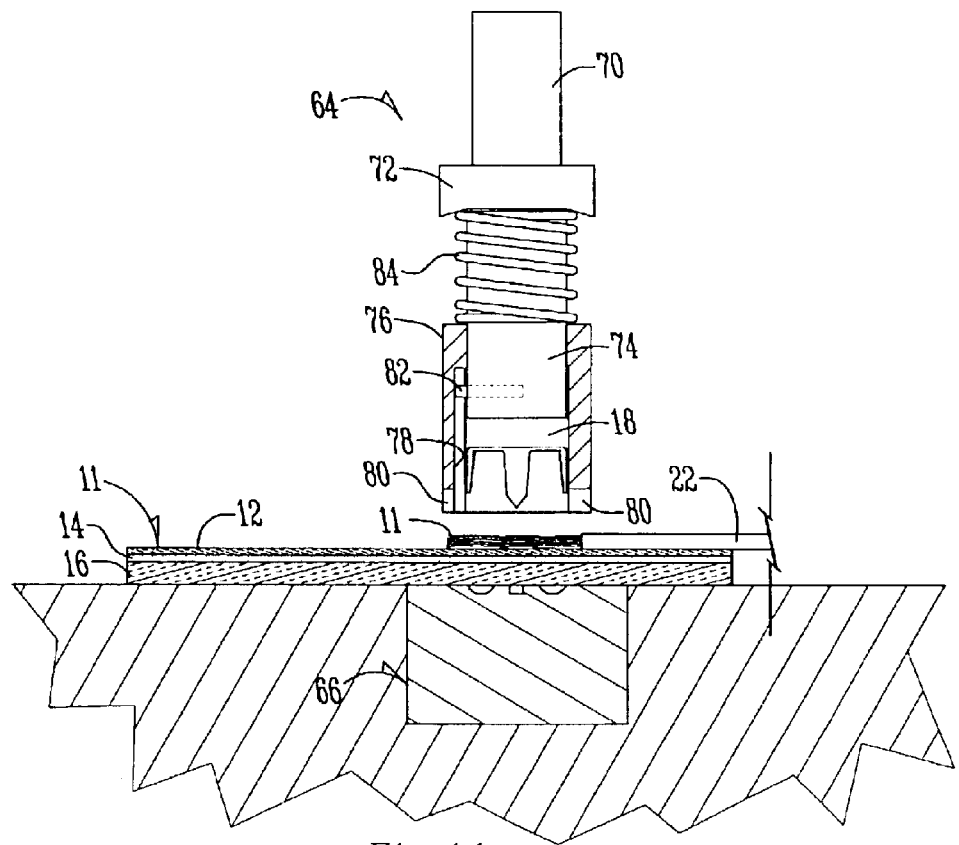
FIG. 11 is an enlarged detailed sectional view of the dies shown in FIG. 10.
Figure 12:
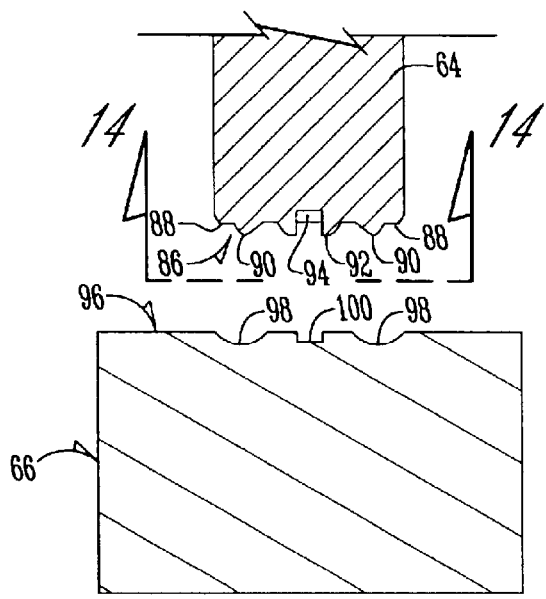
FIG. 12 is an enlarged sectional view showing the two die faces of the machine of FIG. 10.
Figure 13:
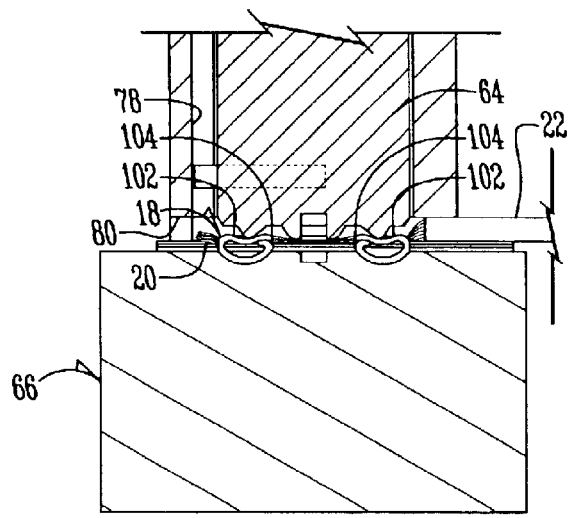
FIG. 13 is a view similar to FIG. 12, but showing the dies in their fully extended position with the electrode clamped therebetween.
Figure 14:
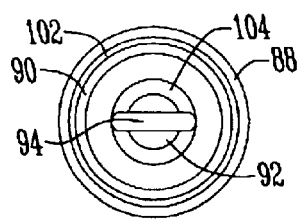
FIG. 14 is a plan view taken along line 14—14 of FIG. 12.

FIGS. 10–14 show the apparatus for applying the connector 18 to the sheet member 11. The apparatus includes a base 54 having a column or mast 56 extending upwardly therefrom. At the upper end of the mast 56 is attached an upper support having a pneumatic cylinder 60 pointed downwardly therefrom. The cylinder 60 includes a cylinder ram 62 having an upper die 64 mounted on the lower end thereof. FIGS. 11–13 show the relationship of the upper die 64 to a lower die 66 which is positioned below it. The details of the upper die surface as shown in FIGS. 12–14 as are the details of the lower die surface 66. The upper die surface 86 includes an outside chamfer 88, a concave ring 90 and a center recess 92. Within the center recess 92 is an elongated wire slot 94. On the opposite edges of the concave bending ring 98 are an exterior ridge 102 and an interior ridge 104. These ridges 102, 104 create the two pinch points 106, 108 (FIG. 4) in the manner described below. The lower die surface is designated by the numeral 96 and includes a concave bending ring 98, a central slot 100.

A wire clamp 68 is provided upon base 54 and clamps the wire 20 to hold it in position over a sheet member 11 also positioned on the upper surface of base 54.

Referring to FIG. 11, the upper die 64 includes a central shaft 70 having a spring stop flange 72 intermediate its opposite ends. Shaft 70 includes a lower end 74 which is surrounded by a sleeve 76. Sleeve 76 on its interior bore has a vertical slot 78 which is open at its lower end and which is closed at its upper end. Sleeve 76 also includes diametrically opposed notches 80 which are aligned with the wire 20 so as to straddle the wire when the device is fully depressed. A pin 82 extends from the lower end 74 of shaft 70 radially outwardly and rides within the vertical slot 78. The pin limits the movement of the sleeve 76 in a downward direction, but permits it to rise against the pressure exerted by a spring 84.

Inserted with the bore of sleeve 76 is a connecting device 18 which is of the structure shown in FIGS. 7–9. The upper surface of the connector 18 rests against the upper die surface 86, and the shape of the upper die surface 86 conforms to the rings 88–90, 92 and the ridges 102, 104 shown in FIG. 14 which have been preformed in the connector 18.

The pneumatic cylinder 60 is actuated to cause the ram 62 to move downwardly. This causes the sleeve to engage the wire 20 and the upper tin surface 12 of the electrode as shown in FIG. 13. In this position the notches 80 of the sleeve straddle the wire 20. The die surface 86 is pressed downwardly on the upper surface of the connector 18.

The prongs 28, 32, 38 and 40 engage the concave bending ring 98 of the lower die 66. The concave surfaces of these rings 98 cause the prongs to bend inwardly and ultimately to begin bending upwardly. This action causes the prongs 28, 30 to pierce the layer 11 through pierce holes 51, 53 as shown in FIG. 4. Similarly the concave surfaces of rings 98 cause the third and fourth prongs 38, 40 to bend in a similar manner to pierce the layer 11 at piercing holes 48–50. Because of the longer lengths and profile of the third and fourth prongs 38, 40, the tips 42 of those prongs protrude upwardly through the central body opening 26 and are bent over to engage the tops of the central portion 24 of connector 18.

However, as shown in FIG. 4 the shorter lengths of the prong pairs 28, 30 cause them to be bent beneath the central portion 24 as shown in FIG. 4.

The ridges 102, 104 of the upper die 64 press downwardly to create the two concentric pressure points 106, 108 shown in FIG. 4. They also press downwardly to force the tips 42 of the third and fourth prongs 38, 40 to be bent downwardly against the upper surface of the connector 18.

The present invention forces the wire 20 into direct positive engagement with the tin surface 12 of the layer 11. The connector 18 forces the wire downwardly into contact with this tin surface 12 in two different concentric places 106, 108 as shown in FIG. 4. The wire rises upwardly through the central opening 26 of the connector 18, and the wire slot 94 in the die surface 86 helps accommodate this risen portion.

The connector 18 provides very great pull strength in the event that the wire 20 is pulled away from the connector.

There are four pressure points at 106, 108 that grip the wire and hold it in positive contact with the tin surface 12. Furthermore, the inwardly pinched prong pairs 28, 30 provide a further attachment of the wire, and resist longitudinal pulling of the wire.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention as further defined in the following claims.

What is claimed is:

1. An electrode comprising
    a laminated sheet having a hydrogel layer of tacky electrically conductive material, an electrically conductive layer, and one or more additional layers, said conductive layer being between said hydrogel layer and said additional layers and being in electrical contact with said hydrogel layer;
    a rigid body having a first body surface facing said conductive layer of said laminated sheet, a second body surface opposite from said first body surface, first and second opposite body edges, and a body opening between said first and second opposite body edges;
    said body having a first pair of prongs, a second pair of prongs, a third prong, and a fourth prong extending therefrom;
    a wire having a bare wire portion free from insulation positioned between said first body surface of said body and said conductive layer of said laminated sheet and being in electrical contact with said conductive layer of said laminated sheet;
    said bare wire portion extending across said body opening and being positioned between said first pair of spaced apart prongs and also between said second pair of spaced apart prongs;
    said first and second pairs of prongs and said third and fourth prongs each piercing in a first direction through said conductive layer and said additional layers, and then piercing in a second direction opposite from said first direction through said additional layers and said conductive layer and contacting said rigid body to attach said bare wire portion in electrical contact with said conductive layer.

2. Apparatus according to claim 1 wherein first surface of said body includes a first convex surface on one side of said body opening and a second convex surface on the opposite side of said body opening, said first and second convex surfaces pressing said wire into contact with said conductive layer at spaced apart first and second pressure points respectively.

3. Apparatus according to claim 1 wherein said body is circular in shape.

4. Apparatus according to claim 3 wherein said body opening is circular in shape.

5. Apparatus according to claim 1 wherein said body is non circular in shape.

6. Apparatus according to claim 1 wherein said first and second pairs of prongs each includes a prong end contacting said first body surface.

7. Apparatus according to claim 6 wherein said third and fourth prongs each includes a prong end extending within said body opening and contacting said second body surface.

8. Apparatus according to claim 1 wherein said first and second pairs of prongs each include a pair of prong ends that straddle said bare wire portion and then pinch toward one another and cover at least a part of said bare wire portion.

9. In combination:
- a sheet member having an electrically conductive sheet member and a hydrogel layer in electrical contact with said conductive sheet member;
- a body having a first body surface facing said conductive sheet member, and having a second body surface opposite from said first body surface, first and second opposite body edges, and a body opening between said first and second opposite body edges;
- said body having first and second pairs of prongs extending therefrom;
- a wire having a bare wire portion free from insulation positioned between said first body surface and said sheet conductive member and being in electrical contact with said conductive sheet member;
- said bare wire portion extending across said body opening and being positioned between said first pair of spaced apart prongs and also between said second pair of spaced apart prongs;
- said first and second pair of spaced apart prongs extending through said conductive sheet member and attaching said body to said conductive sheet member with said wire between said body and said conductive sheet member.

10. A combination according to claim 9 wherein said body includes spaced apart first and second convex surfaces pressing said bare wire portion into contact with said sheet member to create two spaced apart contact points between said wire and said sheet member.

11. A combination according to claim 10 wherein said first and second convex surfaces are positioned on opposite sides of said body opening.

12. A combination according to claim 9 wherein said first and second pairs of prongs each include a pair of spaced apart prong ends on opposite sides of said bare wire portion.

13. A combination according to claim 12 wherein said prong ends of said first pair of prongs are pinched toward one another and said prong ends of said second pair of prongs are pinched toward one another to hold said wire in contact with said sheet member.

14. A combination according to claim 9 wherein said body comprises a third prong and a forth prong, said third and forth prongs piercing said sheet member and each having a prong end bent over said second surface of said body to further attach said body to said sheet member.

15. A method for assembling and electrode comprising:
- taking a connector body having a central portion comprising a first body surface, a second opposite body surface, a body opening extending there through, a first body edge on one side of said opening and a second body edge on the opposite side of said opening, said body member having a first pair of prongs and a second pair of prongs each extending therefrom and each terminating in a spaced apart pair of prong ends;
- placing a bare wire free from insulation between said spaced apart prongs of said first and second pairs of prongs and in electrical contact with a conductive layer of a sheet member;
- piercing said prong ends of said first and second pairs of prongs in a first direction through said sheet member so that said bare wire is between, and in electrical contact with, said conductive layer of said sheet member and said first surface of said connector body;
- piercing said prong ends of said first and second pairs of prongs in a second direction opposite from said first direction through said sheet member so that said prong ends of each of said first and second pairs of prongs are on opposite sides of said bare wire; and
- pressing said prong ends of said first and second pairs of prongs against said central portion of said connector body to attach said wire to said sheet member in contact with said top surface of said sheet member.

16. A method according to claim 15 wherein a third prong and a fourth prong extend from said connector body, said method further comprising piercing said third and forth prongs in said first direction through said sheet member to further secure said connector body, said bare portion of said wire and said conductive layer together.

17. A method according to claim 16 and further comprising piercing said third and forth prongs in said second direction through said sheet member to further secure said connector body, said bare portion of said wire and said conductive layer together.

* * * * *